US006379613B1

(12) United States Patent
Stempf

(10) Patent No.: US 6,379,613 B1
(45) Date of Patent: Apr. 30, 2002

(54) AUTOCLAVE

(76) Inventor: Christian Stempf, 5 Chemin du Crosillon, F-67100 Strasbourg (FR)

( * ) Notice: Subject to any disclaimer, the term of this patent is extended or adjusted under 35 U.S.C. 154(b) by 0 days.

(21) Appl. No.: 09/410,117

(22) Filed: Sep. 30, 1999

(30) Foreign Application Priority Data

Oct. 5, 1998 (EP) .............................. 98890285

(51) Int. Cl.⁷ ................................................ A61L 2/08
(52) U.S. Cl. ........................... 422/26; 422/26; 422/33; 422/298; 122/35; 122/235.29; 122/488; 122/489; 122/492
(58) Field of Search ............................ 422/26, 33, 298; 122/35, 235.29, 488, 489, 492

(56) References Cited

U.S. PATENT DOCUMENTS

| 3,884,636 | A |   | 5/1975  | Knoblauch et al. ............ 21/94 |
|-----------|---|---|---------|-------------------------------------|
| 4,241,010 | A | * | 12/1980 | Baran .......................... 422/28 |
| 4,261,950 | A | * | 4/1981  | Bainbridge et al. ........... 422/28 |
| 4,457,892 | A | * | 7/1984  | Young ......................... 422/33 |
| 4,623,516 | A | * | 11/1986 | Weiler et al. ................. 422/28 |
| 5,068,087 | A | * | 11/1991 | Childers ....................... 422/28 |
| 5,492,672 | A | * | 2/1996  | Childers et al. .............. 422/33 |
| 5,591,396 | A | * | 1/1997  | Chiffon et al. ................ 422/28 |

FOREIGN PATENT DOCUMENTS

| DE | 4211744 | 4/1993 |
| DE | 4312474 | 11/1995 |
| DE | 4445054 | 6/1996 |
| GB | 2131695 | 6/1984 |

* cited by examiner

Primary Examiner—Terrence R. Till
Assistant Examiner—Imad Soubra
(74) Attorney, Agent, or Firm—Friedrich Kueffner

(57) ABSTRACT

The invention concerns a water steam sterilizer, a so-called autoclave which consists of a steam generator (5), a chamber (13), a condenser (19) and a vacuum pump (20), whereby a pipe (9) connects the steam generator (5) with the chamber (13) and a pipe (35) connects the chamber (13) with the steam generator (5), whereby a valve (16) is provided in a pipe (34) between the chamber (13) and the condenser (19).

The autoclav according to the invention is characterised in that valves (10, 17) are provided in the pipe (9) and the pipe (35) respectively.

The invention further relates to a method for steam-sterilizing a load in a chamber.

6 Claims, 1 Drawing Sheet

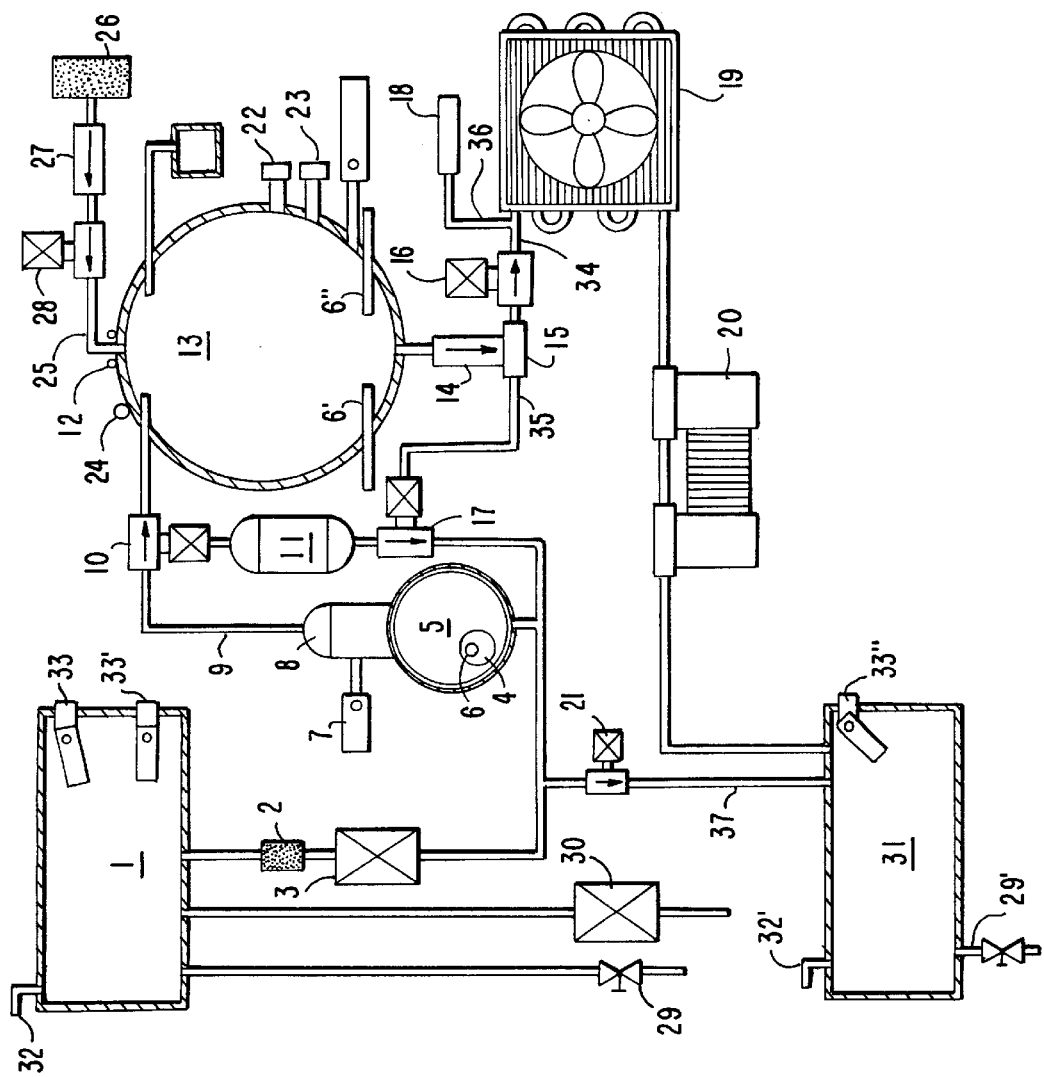

AUTOCLAVE

BACKGROUND OF THE INVENTION

The invention concerns a water steam sterilizer, a so-called autoclave.

Such devices are especially required in the medical field and, because of the constant increasing resistance of germs, must enforce increasingly costlier sterilisation procedures.

Of this fact, considering present days requests, it is absolutely necessary practically world wide that, at the beginning of each sterilisation cycle, the initially existing air in the chamber and the load is essentially completely removed by a specific procedure consisting in successive vacuum and pressure pulses called fractionate vacuum.

This means, that after a first vacuum phase and heating up, steam must be injected in the chamber in order to grow up internal temperature and pressure (>0 bar relative, for practical reasons the pressure is always given in relation to the atmospheric pressure). Then the chamber is drained before a successive vacuum phase in initiated. This is repeated a number of times, until the sufficient expulsion of the initial air is guaranteed.

First then the next phase, the initialisation of the sterilisation procedure will start, with more highly than until now reached temperature and corresponding pressure.

It is clear that a longer time is required, also the quantity of the necessary energy as well as the water consumption increase significantly, since several chamber filling and drain are required, without that these can be considered as sterilisation phases.

Also beside the duration, attention must be given in particular to the energy and also the water consumption (main water cannot be used).

An appliance corresponding nearly to this type of technology, is described in the DE 44 45 054 C2. The appliance in accordance to this document uses a non water cooled condenser and also a water free working vacuum pump.

By the way, it fulfills some of the above mentioned conditions. The disadvantage of this appliance, which however is not detailed in the specified document, is that during the starting, between each vacuum and pressure pulse (phase), not only the chamber is drained, but also the steam generator.

This means that, firstly a big quantity of water and energy required to generate steam is wasted, and secondly a corresponding time is necessary to rebuilt steam and reach again the process parameter for the next pressure pulse.

Of course, it is possible to reduce the time losses by using powerful heating systems, however this changes nothing regarding energy and water losses or better to say wasting.

SUMMARY OF THE INVENTION

Consequently, the goal of the invention is to provide an autoclave, and its principle of functioning, avoiding the listed disadvantages and able to manage the predetermined vacuum and pressure pulses using less water and energy, this without increasing the duration of the cycle.

Due to the invention, the goals are reached principally by using valves placed between the chamber and the steam generator and between the chamber and the condenser/vacuum pump group. During the chamber drain phases, the valves insulate completely the chamber from the steam generator in order not to drain it and that the air/steam/water mixture crosses the condenser and the vacuum pump, before to be drained in the used water tank.

As vacuum pump, preferably a membrane vacuum pump is used due to its ability to suck air, steam or water as well as any air/steam/water mixture.

In an preferred embodiment. The device is additionally equipped with a so called condensation accumulator in order to extract the condensed steam (water) from the chamber and at regular intervals drain it in the steam generator to be heated up again.

BRIEF DESCRIPTION OF THE DRAWING

The invention is explained more in details with the enclosed diagram. This unique diagram describes a schematic representation of the fluid circulation of an autoclave according to the invention.

DESCRIPTION OF PREFERRED EMBODIMENTS

The combination condenser and vacuum pump is used in following way. During the first vacuum pulse (cold start) the membrane vacuum pump sucks only air without water. For the other pulses, the vacuum allowing to suck the air/steam/water mixture, is principally produced by the condenser, the volume of the steam been reduced to the corresponding water volume (reduction 1700/1).

The consequence is that at a certain vacuum level, the efficiency of the membrane pump would be lower than the condenser ones. Both working one against the other and the effect would be that water remains inside the condenser, fills it progressively and reduces distinctly it's efficiency (reduction) so that the pre-set vacuum could not been reached.

To avoid this effect, to ensure a continuous drain of the water and to keep the maximum efficiency of the condenser, a calibrated quantity of air is introduced upstream the condenser but downstream the autoclave chamber allowing the vacuum pump to suck out the water and drain the condenser continuously.

It should be understood that the vacuum level, the duration of successive vacuum pulses and thereby the efficiency are in direct proportion to the size of the condenser (if drained) and not to the flow rate of the vacuum pump. The vacuum pumps flow rate influences only the duration of the first vacuum pulse without water (cold start), for which a longer time would be necessary by using a smaller, but economical pump.

As may be seen from the figure, the invention provides an autoclave with the following features:

The process water, taken from a tank 1 through a filter 2, is injected by a pump 3 in a steam generator 5. The steam generator 5 is equipped with an eccentric positioned heating element 4 and a temperature sensor 6.

A safety valve 7 is connected to the steam generator. A tube 9 links the steam dome 8 of the generator 5 to a three way valve 10 and depending of it's position, to the chamber 13 or the condensation accumulator 11.

When the three way valve 10 is switched, the steam reaches the chamber 13 and the pressure in the chamber increases. When the chamber 13 is drained, the steam streams through a one way valve 14, an embranchement 15, through a tube 34 and a drain valve 16 to a condenser 19 and is pumped off by the vacuum pump 20 into a waste tank 31.

During the pressure pulses and the sterilization process, the drain valve 16 is kept closed and the chamber is connected to the condensation collector 11 through branching 15 to a tube 35 to another three way valve 17, which position in these phases depends of the position of the above mentioned three way valve 10. The condensation collector 11 is directly linked to the chamber but it's temperature is lower. This "cold point" creates a physical phenomenon similar to a little vacuum, sucking out the condensation from the chamber 13. From here it is discharged in regular intervals into the steam generator 5 to be heated up again. This process according to the invention saves water, energy and time.

An air-inlet-valve 18 is connected to the pipe 34 downstream of the valve 15 but upstream of the condenser 19. Through this valve 18 and its pipe 36, a precisely predetermined quantity of air is added to the condensor-bound steam for two reasons: Firstly to obtain a perfect and continuous drain of the condenser and secondly to allow the membrane pump 20 to suck directly water thereby guaranteeing a low noise level.

Of course these so called "vacuum losses" are therefore determined in relation to the flow rate of the membrane pump 20 in a way to reach easily the predetermined optimal values in all the vacuum phases.

In the meantime, during the vacuum phases, it is possible to heat up the steam generator 5 in order to "accummulate" steam for the next pressure pulse. As soon as the pressure in the chamber 13 has dropped to the predetermined value, the drain valve 16 is closed and both three way valves 10 and 17 are so switched that the steam prepared in the steam generator 5 is injected into the chamber 13 and the condensation which has been formed in chamber 13 is extracted and returned through the condensation collector 11 to the steam generator 5, until predetermined pressure and temperature values are reached again in chamber 13.

Having reached this stage, new vacuum/pressure pulses can start, and so on . . .

With the successive vacuum and pressure phases it is possible to reach a residual air percentage of less than 0.1%. In a prefered embodiment, in order to reduce and optimise the duration of the air expulse procedure and the total cycle, a time out has been fixed for the first three vacuum pulses (ex: 3min). If the vacuum pulses do not reach within this time out the predetermined value (ex: 0.80 bar), the maximum negative pressure is registered and the cycle goes on.

At the end of the three pulses, the microprocessor calculates the theoretical complementary vacuum and defines the value of the 4th additional pulse with the registered values so that the theoretical air residual percentage can be reached.

Even after the expulsion of the air by the fractionate vacuum, during the build-up of the pressure and sterilization phases, the condensation has to be regularly drained from the chamber 13. In order to achieve this, both three way valves 10 and 17 are switched in a position which, as explained before, separates the chamber 13 completely from the steam generator 5 and leads the condensation to the condensation collector 11.

The additional advantages of this part of the invention are that the chamber 13 and especially its content, the load, remains even during the pressure pulse as dry as possible, which brings a reduction of the condensation passing through the condenser 19 and the vacuum pump 20 during the vacuum phase. All such condensation heats them up and reduces needless their efficiency, so any reduction of condensation passing through the condenser and the vacuum pump is a valuable progress.

Further, the dry state of the chamber 13 and its load improves the drying process and reduces its duration.

So, the invention allows for a perfect obeyance of the well known imperative: "To get a perfect drying, avoid to moisten the load".

During the drying phase, the internal temperature of the steam generator 5 shall be reduced to about 105° C. which allows for a direct draining by opening the waist valve 21 leading to the waste tank 31 without cooling the steam.

Additionally to the described components and pipes appropriate in the described preferred embodiment of the invention, the drawing still discloses other features, elements and parts:

The chamber 13 is provided with two temperature sensors 6' and 6" in order to obtain, at each phase of the process-cycle, with sufficient reliability the temperature prevailing in the chamber. For checking and surveillance purposes, connections 22 for a pressure test and 23 for a temperature test can be used. The chamber 13, having a thermal insulation, is heated by an external heating element 12, which temperature is controlled by an external sensor 24 completely independently from the internal ones.

In order to introduce external sterile air, the chamber 13 is connected to an air inlet by a tube 25, through a valve 28, a one way valve 27 and a bacteriological filter 26. It is necessary, at the end of the sterilization process, to equilibrate the chamber to the atmospheric pressure prior to the opening of the door.

To the emptying of both tanks 1 and 31, drain cocks are foreseen respectively 29 for the pure water, and 29' for the waste. Additionally, a connection to an external pure water tank is provided in a way to have an automatic refilling of the pure water tank 1 by a water pump 30. Both tanks 1 and 31 are most completely watertight and need external connections 32 and 32'.

The tanks are equipped with water level sensors 33, 33' and 33", in order to prevent under- or overfilling. The condenser 19 is air cooled but a water cooled condenser can be used without altering the generic concept of the invention or leaving its scope. The represented membrane pump 20 can be replaced by any other pump used for such application.

In the drawing, the pipes are shown in a purely schematic manner, it is clear for the man skilled in the art that various details, which are not part of the invention have to be taken into account. The position of the parts relative to each other, the necessity to use further pumps or different heights of the parts in order to provoke a natural circulation and all mechanical features have no room on a fluid diagram which the drawing is.

Similarly, all kind of materials and the electronic control means have not been discussed, because it is clear for the man skilled in the art that the materials and the electronics usually used in connection with autoclave can be used for the invention too.

Naturally, it is preferred to have a full-automatic autoclave which only has to be loaded and unloaded and detects all kind of failures by itself, stops its functioning and gives the pertinent messages, but it is clear that a "manual handling" is possible too.

As it becomes clear from the description, it is one of the main features, if not the main feature, of the invention to re-use the condensation by recycling it from the chamber to the steam generator, eventually via a condensation collector, and not to waste it.

What is claimed is:
1. Method for steam-sterilizing a load in a chamber (13), including the steps:

a) connecting the chamber with a vacuum pump (20) and reducing the pressure in the chamber, forcing out an essential part of the initially enclosed air, b) shutting the connection between the chamber (13) and the vacuum pump (20) and connecting the chamber with a steam generator (5), building up the pressure and temperature in the chamber up to a first predetermined value, c) shutting the connection between the chamber (13) and the steam generator (5) and connecting the chamber with a condenser (19), decreasing the pressure and temperature in the chamber and forcing out further essential parts of the initially enclosed air, d) eventually repeating the steps b) and c) until the originally enclosed air is forced out essentially totally, but with the provision for step b) that the connection between the chamber (13) and the condenser (19) is shut too, e) shutting the connection between the chamber (13) and the vacuum pump (20) and connecting the chamber with a steam generator (5), building up the pressure and temperature in the chamber up to a second, predetermined value, the process value, which is greater than said first predetermined value, f) shutting the connection between the chamber (13) and the steam generator (5) and connecting the chamber with a condenser (19), decreasing the pressure and temperature in the chamber, g) shutting all connections from the chamber to the steam generator, the condensor and the vacuum pump and opening an air inlet (26) in order to achieve a pressure equilibrium of the chamber with the outside, opening the chamber and taking out the sterilized load, wherein at least during and/or after one of the steps b) and/or e) condensation from the chamber (13) is drained directly or via a condensation collector (11) to the steam generator (5).

2. Method according to claim 1, wherein a time out has been fixed for the first three vacuum pulses of steps b) and c) and, if the vacuum pulses do not reach within this time out the predetermined negative pressure value, the maximum negative pressure is registered and the cycle goes on and, at the end of the three pulses, a microprocessor calculates the theoretical complementary vacuum and defines the value of a fourth additional vacuum pulse with the registered negative pressure value so that a theoretical air residual percentage can be reached.

3. An autoclave comprising:

a steam generator (5) having a steam dome (8);

a chamber (13) having an upper end and a lower end;

a condenser (19);

a vacuum pump (20);

a first pipe (9) connecting the steam dome (8) of the steam generator (5) with the upper end of the chamber (13);

a second pipe (35) connecting the lower end of the chamber (13) with the steam generator (5);

a third pipe (34) connecting the lower end of the chamber (13) with the condenser (19);

a valve (16) provided in the third pipe (34) between the chamber (13) and the condenser (19);

valves (10, 17) provided in the first pipe (9) and the second pipe (35), respectively;

a condensation collector (11) connected, parallel to the chamber (13), to the first pipe (9) and to the second pipe (35), respectively, wherein at least one of the connections to the first pipe (9) and to the second pipe (35) is provided with a valve.

4. An autoclave according to claim 3, wherein the valves (10, 17) provided in the first pipe (9) and the second pipe (35, are three-way-valves and the condensation collector (11) is connected to the first and second pipes (9, 35) by said valves (10, 17).

5. An autoclave according to claim 3, comprising an air inlet (18) which is calibrated and can be shut off, wherein the air inlet is provided between the condenser (19) and the valve (16) provided in the third pipe (34).

6. An autoclave according to claim 3, wherein the steam generator has a waste-condensation outlet (37) which can be shut off.

* * * * *